(12) United States Patent
Porges et al.

(10) Patent No.: US 8,915,249 B2
(45) Date of Patent: Dec. 23, 2014

(54) SYSTEMS AND METHODS FOR CONSERVING OXYGEN IN A BREATHING ASSISTANCE DEVICE

(75) Inventors: Charles E. Porges, Orinda, CA (US); Joseph Douglas Vandine, Manteca, CA (US)

(73) Assignee: Chart Inc., Ball Ground, GA (US)

( * ) Notice: Subject to any disclaimer, the term of this patent is extended or adjusted under 35 U.S.C. 154(b) by 945 days.

(21) Appl. No.: 13/120,461

(22) PCT Filed: Aug. 28, 2009

(86) PCT No.: PCT/US2009/055289
§ 371 (c)(1),
(2), (4) Date: Oct. 11, 2011

(87) PCT Pub. No.: WO2010/036479
PCT Pub. Date: Apr. 1, 2010

(65) Prior Publication Data
US 2012/0017909 A1    Jan. 26, 2012

Related U.S. Application Data

(60) Provisional application No. 61/099,393, filed on Sep. 23, 2008.

(51) Int. Cl.
| | |
|---|---|
| A62B 7/00 | (2006.01) |
| A62B 9/00 | (2006.01) |
| A61M 16/00 | (2006.01) |
| G05B 1/00 | (2006.01) |
| F16K 31/02 | (2006.01) |
| A61M 16/12 | (2006.01) |
| A61M 16/10 | (2006.01) |

(52) U.S. Cl.
CPC ....... *A61M 16/12* (2013.01); *A61M 2202/0208* (2013.01); *A61M 2016/0039* (2013.01); *A61M 2016/0027* (2013.01); *A61M 2205/50* (2013.01); *A61M 16/125* (2013.01); *A61M 16/0069* (2013.01); *A61M 2205/581* (2013.01); *A61M 2205/52* (2013.01); *A61M 16/1015* (2013.01)
USPC ............. 128/205.11; 128/204.22; 128/204.23

(58) Field of Classification Search
CPC . A61M 16/00; A61M 16/10; A61M 2205/33; A61M 2205/50
USPC ............. 128/204.18, 204.21–204.23, 204.26, 128/205.11, 203.25
See application file for complete search history.

(56) References Cited

U.S. PATENT DOCUMENTS 5,239,994 A * 8/1993 Atkins ...................... 128/204.18
6,192,884 B1 * 2/2001 Vann et al. ................ 128/204.26
(Continued)

FOREIGN PATENT DOCUMENTS

| EP | 1205203 A2 | 5/2002 | ............ A61M 16/00 |
|---|---|---|---|
| EP | 1579883 A2 | 9/2005 | ............ A61M 16/00 |

(Continued)

OTHER PUBLICATIONS

International PCT Search Report, PCT/US2009/055289, 5 pages.

*Primary Examiner* — Kristen Matter
(74) *Attorney, Agent, or Firm* — Mintz Levin Cohn Ferris Glovsky and Popeo, P.C.

(57) ABSTRACT

A system and method for conserving oxygen in a breathing assistance device are disclosed. A method may include delivering breathable gas with a first average oxygen concentration during a first portion of an inhalation phase for a patient. The method may also include delivering breathable gas with a second average oxygen concentration during a second portion of an inhalation phase for a patient.

31 Claims, 3 Drawing Sheets

(56) References Cited

U.S. PATENT DOCUMENTS

2006/0213519 A1* 9/2006 Schmidt et al. .......... 128/204.23
2007/0017520 A1* 1/2007 Gale et al. ................ 128/204.26

FOREIGN PATENT DOCUMENTS

| WO | 2005/118038 A2 | 12/2005 | ............ A61M 16/00 |
| WO | 2009/123977 A1 | 10/2009 | ............ A61M 16/00 |

* cited by examiner

SYSTEMS AND METHODS FOR CONSERVING OXYGEN IN A BREATHING ASSISTANCE DEVICE

CROSS-REFERENCE TO RELATED APPLICATIONS

This application is a U.S. National Stage Application of International Application No. PCT/US2009/055289 filed Aug. 28, 2009, which designates the United States of America, and claims priority to U.S. Provisional Application No. 61/099,393 filed Sep. 23, 2008. The contents of which are hereby incorporated by reference in their entirety.

TECHNICAL FIELD

The invention relates to breathing assistance devices (e.g., ventilators or CPAP devices), and more particularly to systems and methods for conserving oxygen in a breathing assistance device.

BACKGROUND

A breathing assistance device typically delivers pressurized breathable gas to a patient via tubing called a "patient interface" or "breathing circuit." The breathable gas typically includes air and/or one or more additional or supplemental gases (e.g., supplemental oxygen mixed with air). The breathing assistance device typically increases the pressure in the breathing circuit to push the breathable gas into the lungs for inspiration, and reduces the pressure in the breathing circuit to allow gases in the lungs to be expired and vented to the atmosphere. Typically, one or more breathing assistance device parameters may be determined and/or adjusted prior to and/or during operation. Such parameters may include, for example, the mode of ventilation (e.g., CMV (controlled mandatory ventilation), SIMV (synchronized intermittent mandatory ventilation), CPAP (constant positive airway pressure), or bi-level CPAP); the patient's tidal volume (the volume of gas inspired with each breath); the respiratory rate (the number of breaths per minute (BPM)); and/or the $O_2$ concentration, flow rate, airway pressure, and/or minute volume (the volume inspired and expired in one minute) of breathable gas delivered to the patient.

During inhalation, gas inhaled by a patient typically passes through the patient's airway and enters the alveoli of the patient's lungs, where pulmonary gas exchange may take place. Pulmonary gas exchange is driven by passive diffusion, whereby highly-concentrated oxygen moves from the alveoli to the patient's blood stream, which typically has a lower oxygen concentration due to the continuous consumption of oxygen in the body. Conversely, the patient's metabolism may produce a higher concentration of carbon dioxide than that of the alveoli, causing diffusion of carbon dioxide from the blood stream to the alveoli, which may then exhaled by the patient.

As mentioned above, the breathable gas delivered by a breathing assistance device typically includes air and/or one or more additional or supplemental gases. In many applications, supplemental oxygen may be mixed with pressurized air to deliver a desired concentration of oxygen to a patient. Alternatively, pure oxygen may delivered to a patient.

Because gas inhaled during the beginning of an inhalation phase is more likely to reach the alveoli (as compared with gas inhaled later during the inhalation phase), oxygen present in such gas is more likely to diffuse into the bloodstream. Gas inhaled during the later portions of the inhalation phase may not diffuse as effectively into the alveoli, and thus oxygen present in such gas may not enter the bloodstream, and may instead be expired by the patient. Accordingly, in applications in which supplemental oxygen is used, the supplemental oxygen delivered during latter portions of an inhalation phase may be, in effect, wasted.

SUMMARY

In accordance with the teachings of the present disclosure, disadvantages and problems associated with oxygen delivery in a breathing assistance system may be substantially reduced or eliminated.

In accordance with one embodiment of the present disclosure, a breathing assistance device may include a gas delivery system, a patient interface, a connection system, and a control system. The gas delivery system may be configured to supply breathable gas. The patient interface may be configured to interface with a patient for delivering breathable gas to one or more breathing passages of the patient. The connection system may be configured to communicate breathable gas supplied by the gas delivery system to the patient interface for delivery to the patient. The control system may be configured to control the delivery of breathable gas to the patient. In addition, the gas delivery system may be configured to deliver breathable gas with a first average oxygen concentration during a first portion of an inhalation phase for the patient. Further, the gas delivery system may be configured deliver breathable gas with a second average oxygen concentration during a second portion of the inhalation phase for the patient, wherein the second average oxygen concentration is lower than the first average oxygen concentration.

In accordance with another embodiment of the present disclosure, a method for delivering breathable gas to a patient is provided. The method may include delivering breathable gas with a first average oxygen concentration during a first portion of an inhalation phase for a patient. The method may also include delivering breathable gas with a second average oxygen concentration during a second portion of an inhalation phase for a patient.

Other technical advantages will be apparent to those of ordinary skill in the art in view of the following specification, claims, and drawings.

BRIEF DESCRIPTION OF THE DRAWINGS

A more complete understanding of the present embodiments may be acquired by referring to the following description taken in conjunction with the accompanying drawings, in which like reference numbers indicate like features, and wherein.

DETAILED DESCRIPTION

Embodiments of the disclosure are best understood by reference to FIGS. 1 through 6, wherein like numbers are used to indicate like and corresponding parts.

Figure 1:
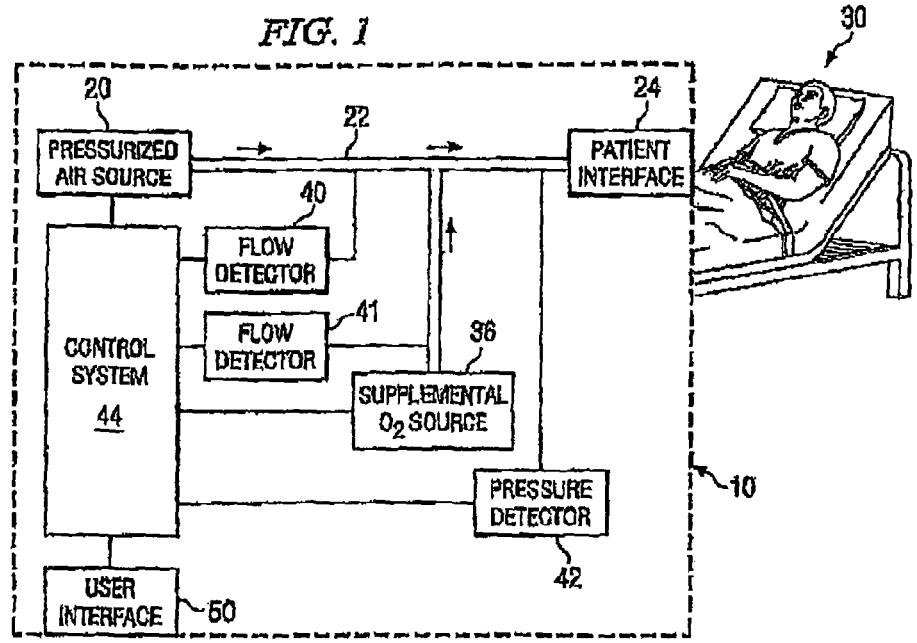
FIG. 1 illustrates a block diagram of an example breathing system having oxygen conservation functionality in accordance with the present disclosure.

FIG. 1 illustrates a breathing assistance device 10 having oxygen conservation functionality in accordance with one embodiment of the disclosure. In general, the oxygen conservation functionality may permit a greater concentration of oxygen to be delivered during a first portion of a patient inhalation relative to a second portion of the patient inhalation.

As used herein, the terms "gas" and/or "breathable gas" may refer to any one or more gases and/or vaporized substances suitable to be delivered to and/or from a patient via a tracheal tube, endo-tracheal tube, and/or one or more breathing orifices (e.g., the nose and/or mouth), and may include air, nitrogen, oxygen, any other component of air, $CO_2$, vaporized water, vaporized medicines, nebulized medicines, and/or any combination of two or more of the above, for example.

As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

As shown in FIG. 1, breathing assistance device 10 may include an pressurized air source 20, a connection system 22, a patient interface 24, supplemental oxygen source 36, flow detectors 40 and 41, a pressure detector 42, a control system 44, and a user interface 50. Pressurized air source 20 may comprise any system or device suitable for generating and/or delivering pressurized gas (e.g., air and/or supplemental oxygen) toward a patient 30, including without limitation, a blower, a compressor, a piston-based device, one or more pressurized gas tanks, one or more gas lines (e.g., from a wall or other source), or any combination thereof. Further, in embodiments with one or more gas lines supplying gas to breathing assistance device 10, pressurized air source 20 may comprise one or more valves (e.g., solenoid or other valves) configured to control the flow and/or pressure of air delivered towards patient 30.

Breathing assistance device 10 may also include supplemental oxygen source 36. Supplemental oxygen source 36 may generally be operable to provide a supply of oxygen to patient 30 supplemental to the pressurized air provided by pressurized gas source 20, as described in greater detail below with respect to FIG. 2.

Connection system 22 may include any system or device suitable for delivering pressurized gas from pressurized air source 20 towards patient 30, e.g., a connection system and/or other conduits and connection devices. In some embodiments, connection system 22 may include a proximal pressure line operable to detect gas pressure near patient 30 in connection system 22 or patient interface 24. Patient interface 24 may include any system or device suitable for further delivering pressurized gas delivered by connection system 22 to patient 30, e.g., a nasal or face mask, nasal pillows, and/or a tube (e.g., an endotracheal tube, a tracheostomy tube and/or other tracheal tube).

Each of flow detector 40 and 41 may generally be operable to detect the flow rate of gas flowing through one or more conduits of system 10, e.g., the flow rate produced by pressurized air source 20, supplemental oxygen source 36, and/or the flow rate of gas delivered to patient 30. Flow detector 40 and/or flow detector 41 may include any number of sensors operable to detect flow rate of a gas and/or any device operable to convert a detected flow rate into electrical signals or otherwise sense flow rate. Each of flow detector 40 and flow detector 41 may be placed at any suitable location and in any suitable orientation for sensing flow rate of a gas within breathing assistance device 10. For example, flow detector 40 may be placed within connection system 22, near pressurized air source 20, near supplemental oxygen source 36, an air intake port, and/or an air outlet port.

Pressure detector 42 may generally be operable to detect a pressure of gas within one or more conduits of breathing assistance device 10 by detecting the pressure of gas delivered from source 20, supplemental oxygen source 36, and/or the pressure of gas delivered to patient 30. Pressure detector 42 may include any number of sensors operable to detect gas pressure and/or any suitable device operable to convert a detected pressure into electrical signals or otherwise sense pressure. Pressure detector 42 may be placed at any suitable location and in any suitable orientation for sensing gas pressure within breathing assistance device 10. For example, pressure detector 42 may be placed within connection system 22, near pressurized air source 20, near supplemental oxygen source 36, an air intake port, and/or an air outlet port.

User interface 50 may include any suitable device or devices allowing a user to interface with breathing assistance device 10, e.g., to input desired performance parameters that may be communicated to control system 44 to control the operation of pressurized air source 20 and/or other components of breathing assistance device 10. For example, user interface 50 may allow a user to input one or more of the following performance parameters: the age, weight, tidal volume, respiratory rate, inhale sensitivity, exhale sensitivity, circuit leak, rise time, alarm settings, delay, ramp, starting pressure, inhalation:exhalation (I:E) ratio, and/or other characteristics of patient 30, a desired gas flow rate to patient 30, desired gas pressure or pressures to patient 30, a selected ventilation program, and/or various control (e.g., on/off control or algorithm selection) for the fault detection functionality.

Control system 44 may generally be operable to process various inputs (e.g., input from user interface 50, ventilation programs stored in memory, and/or feedback from flow detector 40, flow detector 41, pressure detector 42, or other variables sensed or otherwise detected by other sensors associated with breathing assistance device 10) and to regulate the operation of pressurized air source 20, supplemental oxygen source 36, and/or other components of breathing assistance device 10 based on such various inputs. Control system 44 may include any suitable system or device for controlling the operation of breathing assistance device 10, including, e.g., a microcontroller, a digital signal processor (DSP), an application specific integrated controller (ASIC), electrically-programmable read-only memory (EPROM), or a field-programmable gate array (FPGA). In some embodiments, control system 44 may include software and/or other executable code for analyzing input signals received from user interface 50 and/or feedback from flow detector 40, pressure detector 42, or other variables sensed or otherwise detected by other sensors associated with breathing assistance device 10 to generate control signals for regulating the operation of breathing assistance device 10. Such software may include any suitable algorithms, logic and/or instructions for processing signals in breathing assistance device 10, and may be stored in any suitable data storage media. In some embodiments, for example those in which control system 44 comprises an FPGA, the functionality of such software may be programmed into the FPGA rather than provided as separate software.

Figure 2:
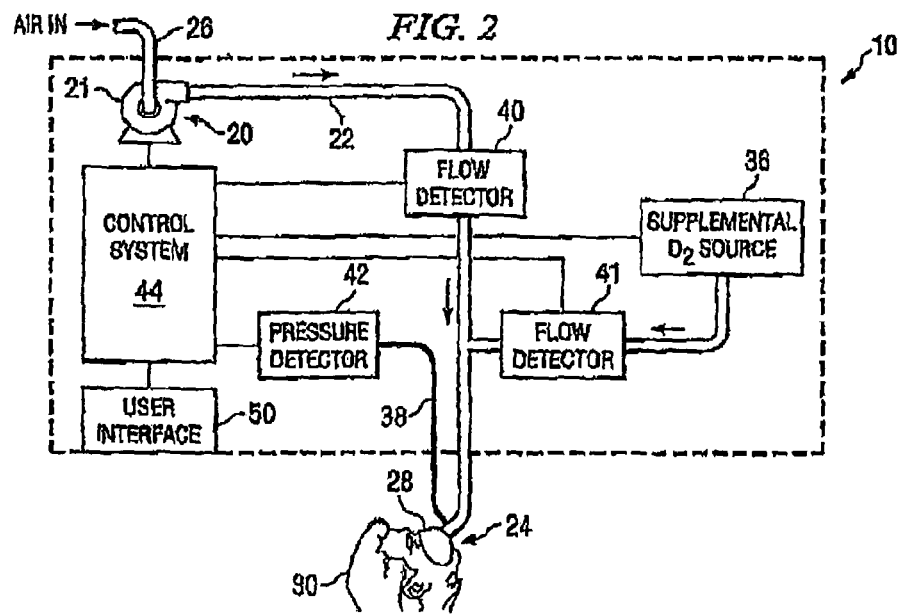
FIG. 2 illustrates an example embodiment of a breathing assistance device having oxygen conservation functionality in accordance with the present disclosure.

In some embodiments, control system 44 controls the operation of pressurized air source 20. For example, where pressurized air source 20 comprises a motorized blower (as shown in FIG. 2) control system 44 may control the operation (e.g., the motor speed and on/off control) of the blower. In addition, control system 44 may control the delivery of oxygen from a supplemental oxygen source (e.g., supplemental oxygen source depicted in FIG. 2).

FIG. 2 illustrates an example embodiment of breathing assistance device 10 having oxygen conservation functionality in accordance with the present disclosure. In this example embodiment, breathing assistance device 10 may include a pressurized air source 20 comprising a motorized blower 21, an air inlet channel 26, a connection system 22, flow detectors 40 and 41, a pressure detector 42, a control system 44, a user interface 50, a pressure line 38, an optional oxygen source 36, and/or a patient interface 24. In some embodiments, breathing assistance device 10 may be a compact, portable breathing assistance device, such as a breathing assistance device for home use. In other embodiments, breathing assistance device 10 may be a larger, more complex breathing assistance device, such as for use in a hospital.

In the embodiment depicted in FIG. 2, pressurized air source 20 may comprise a blower 21 (e.g., a blower having an impeller driven by a motor). Blower 21 may generally be operable to receive atmospheric air from air inlet channel 26, pressurize the air, and deliver the pressurized air through connection system 22.

As discussed above, breathing assistance device 10 may also include supplemental oxygen source 36. Supplemental oxygen source 36 may generally be operable to provide a supply of oxygen to patient 30 supplemental to the pressurized air provided by blower 21. Supplemental oxygen source 36 may be fluidically coupled to connection system 22 and may comprise, e.g., a blower, a compressor, a piston-based device, one or more pressurized gas tanks, or one or more gas lines (e.g., from a wall or other source). Supplemental oxygen source 36 may be placed at any suitable location and in any suitable orientation for providing a supplemental flow of oxygen within breathing assistance device 10. For example, supplemental oxygen source 36 may be physically connected to connection system 22 near patient interface 24 or blower 21, or may be physically connected to air inlet channel 26.

As discussed above, connection system 22 may include any system or device suitable for delivering pressurized gas from blower 21 and/or supplemental oxygen source 36 towards patient 30, e.g., a patient circuit. In some embodiments, connection system 22 may include a proximal pressure line 38 operable to detect gas pressure near patient 30 in connection system 22 or patient interface 24. Patient interface 24 may include any system or device suitable for further delivering pressurized gas delivered by connection system 22 to patient 30. In this example embodiment, patient interface 24 comprises a mask 28, e.g., a nasal mask or a face mask.

Also as discussed above, each of flow detector 40 and flow detector 41 may generally be operable to detect flow rate. For example, flow detector 40 may detect the flow rate of pressurized air delivered from blower 21 to patient 30, and flow detector 41 may detect the flow rate of supplemental oxygen delivered from supplemental oxygen source 36 to patient 30. Each of flow detector 40 and flow detector 41 may include any number of sensors operable to detect gas flow rate and/or any other device operable to convert a detected flow rate into electrical signals or otherwise sense flow rate.

Pressure detector 42 may generally be operable to detect a pressure of gas within one or more conduits of breathing assistance device 10. Furthermore, pressure detector 42 may include any number of sensors operable to detect pressure of a gas and/or any other suitable device operable to convert a detected pressure into electrical signals or otherwise sense pressure. In the embodiment depicted in FIG. 2, breathing assistance device 10 may include a pressure line 38 coupled to pressure detector 42 and operable to communicate a detected pressure (e.g., near blower 21, near supplemental oxygen source 36, within connection system 22, within mask 28, and/or near patient 30) to pressure detector 42.

Also as noted above, user interface 50 may include any suitable device or devices allowing a user to interface with breathing assistance device 10, e.g., to input desired performance parameters that may be communicated to control system 44 to control the operation of blower 21 and/or other components of breathing assistance device 10.

As discussed above, control system 44 may generally be operable to process various inputs, e.g., input from user interface 50, ventilation programs stored in memory, and/or feedback from flow detector 40, flow detector 41, pressure detector 42 or other variables sensed or otherwise detected by other sensors associated with breathing assistance device 10, and to regulate the operation of blower 21, supplemental oxygen source 36, or other components of breathing assistance device 10 based on such various inputs. In some embodiments, control system 44 may control the operation of blower 21 and/or supplemental oxygen source 36. For example, control system 44 may control the motor speed and on/off status of blower 21. Furthermore, control system 44 may generate sound signals to be broadcast breathing assistance device 10, e.g., user feedback (e.g., instructions or other words) and/or other sounds regarding the operation of breathing assistance device 10. For example, control system 44 may monitor the operation of breathing assistance device 10 and, when appropriate, generate alarm signals (e.g., a siren, buzzer, or words) to be broadcast by a sound output device.

In operation, control system 44, in concert with flow detector 40, flow detector 41, and/or pressure detector 42, may determine various parameters associated with a patient's breathing cycle. For example, control system 44 may use flow and/or pressure measurements to determine the beginning and/or end of a breathing cycle, including determining the beginning and/or end of inhalation, determining the beginning and/or end of exhalation, and determining the lengths of time for inhalation and/or exhalation. Based on such parameters, control system 44 may be configured to act in concert with one or more other components of breathing assistance device 10 to deliver a first concentration of oxygen to a patient's airway during a first portion of an inhalation phase of a patient's breath, while delivering a different, second concentration of oxygen to the patient's airway during a second portion of the inhalation phase of the breath, as described in greater detail below. The first portion of the inhalation phase may begin at a time substantially contemporaneous to the beginning of an inhalation, and the first concentration may be greater than the second concentration, such that a lower concentration of oxygen is delivered to the patient near the end of the inhalation phase. Because oxygen delivered to the patient near the end of inhalation is less likely to diffuse into the alveoli of the lungs, reducing the delivered oxygen concentration toward the end of the inhalation phase may conserve of supplemental oxygen.

During inhalation, breathing assistance device 10 may deliver a particular gas flow $F_{tot}$ to a patient over a time $T_{inh}$ as shown in FIGS. 3-6. A portion of the gas delivered may include a flow of supplemental oxygen $F_{oxygen}$, and the remaining portion of the gas delivered may include a flow of pressurized air $F_{air}$, such that $F_{tot}=F_{oxygen}+F_{air}$. The parameters $F_{tot}$, $F_{oxygen}$, and $F_{air}$ may be depend on any number of factors, including without limitation, the patient 30, the lung capacity of patient 30, and the desired oxygenation of patient 30. For example, by appropriately selecting the supplemental oxygen flow and the pressurized air flow (either manually by a person or automatically by control system 44), breathing assistance device 10 may deliver gas with a desired concentration of oxygen to patient 30. As a specific example, if it is desired to deliver gas with a 60.5% oxygen concentration to patient 30, equal parts of supplemental oxygen (oxygen concentration of 100%) and pressurized air (oxygen concentration of approximately 21%) may be delivered to patient 30.

Figure 3:
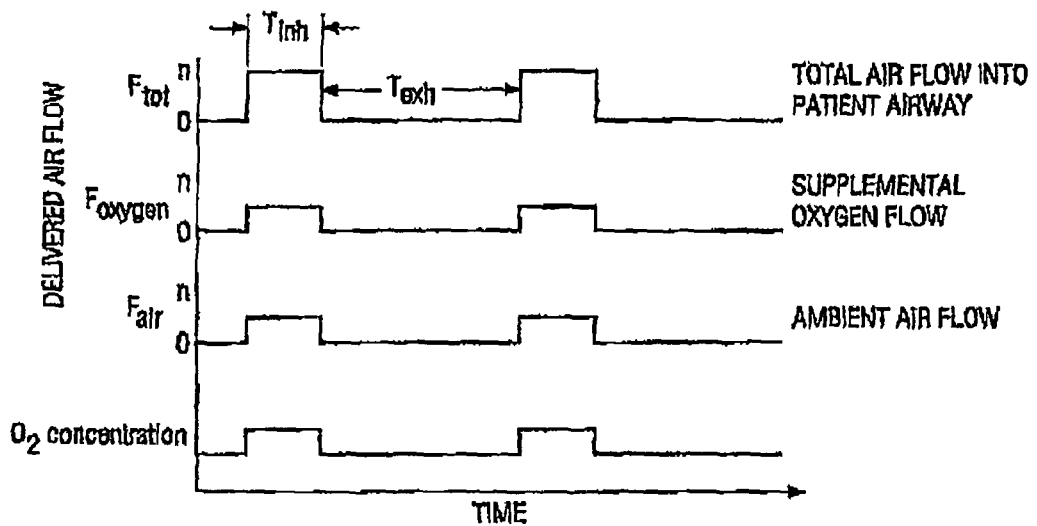
FIG. 3 illustrates a series of graphs depicting the total gas flow into a patient airway and concentration of inspired oxygen during a plurality of breath cycles, including individual flows of supplemental oxygen and pressurized air, according to a conventional approach.

FIG. 3 illustrates a series of graphs depicting the total gas flow into a patient airway and concentration of inspired oxygen during a plurality of breath cycles, including individual flows of supplemental oxygen and pressurized air, according to a conventional approach. As depicted in FIG. 3, under conventional approaches, the ratio of the supplemental oxygen flow $F_{oxygen}$ to the pressurized air flow $F_{air}$ typically remains substantially constant. Accordingly, the oxygen concentration of gas delivered during $T_{inh}$ also remains substantially constant during $T_{inh}$. Because oxygen present in gas inhaled near the end of an inhalation may be less likely to diffuse to the patient's alveoli, the supplemental oxygen component of the gas inhaled near the end of inhalation may go unused and thus be wasted.

Figure 4:
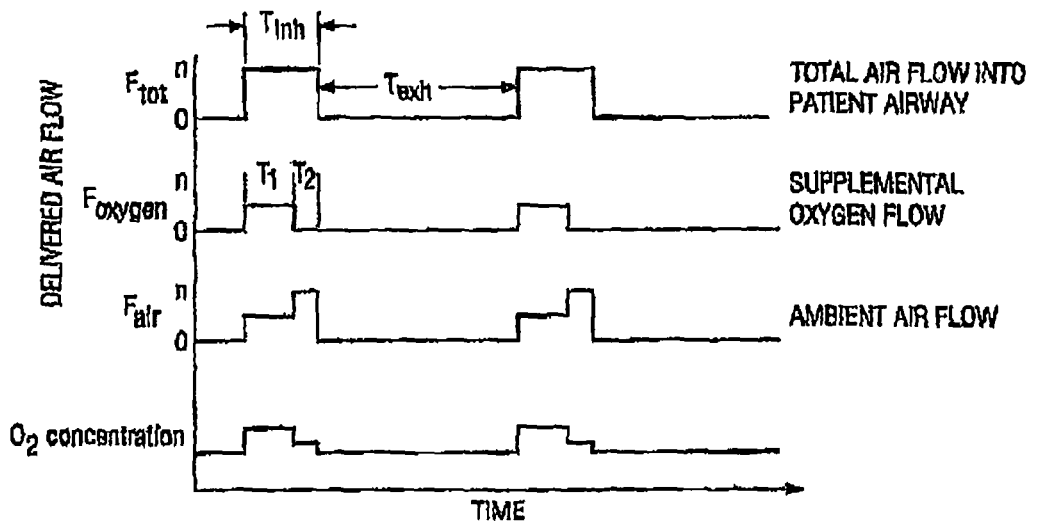
FIGS. 4-6 each illustrate a series of graphs depicting the total air flow into a patient airway and concentration of inspired oxygen during a plurality of breath cycles, including individual flows of supplemental oxygen and pressurized air, in accordance with embodiments of the present disclosure.
Figure 5:
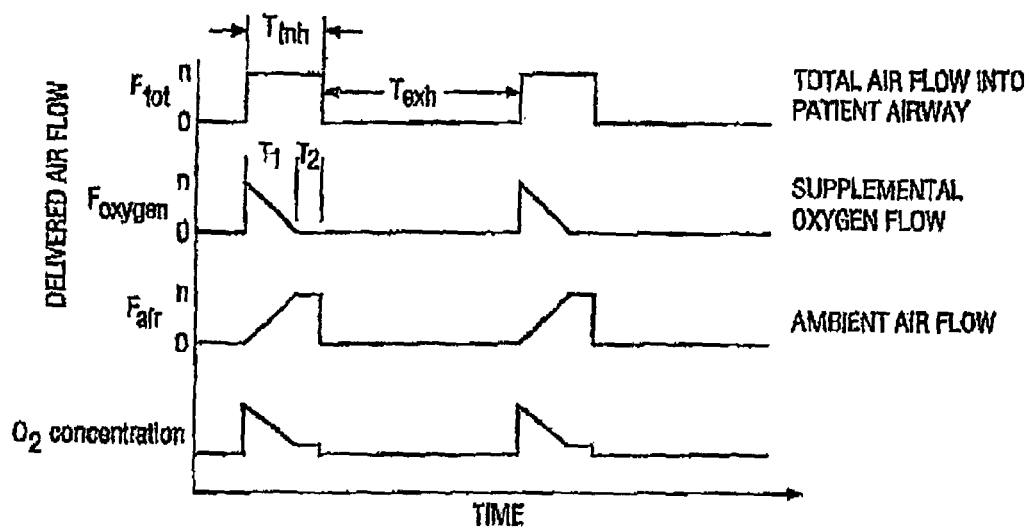
Figure 6:
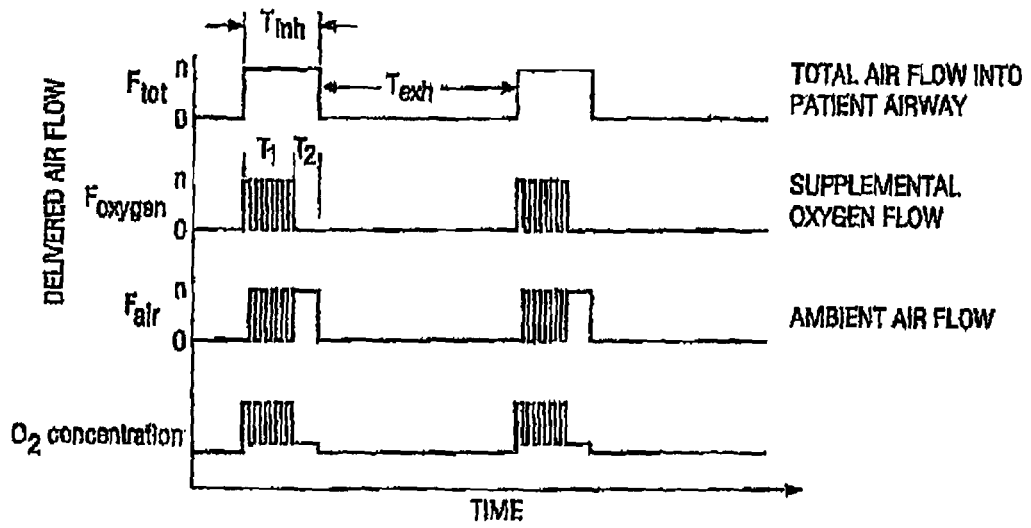

To reduce or eliminate this inefficiency, breathing assistance device 10 according to the present disclosure may be configured such that gas delivered during a first portion of a patient inhalation has a greater oxygen concentration than gas delivered during a second portion of the inhalation, as illustrated by example embodiments depicted in FIGS. 4-6. FIGS. 4-6 each illustrate a series of graphs depicting the total gas flow into a patient airway and concentration of inspired oxygen during a plurality of breath cycles, as well as the component flows of supplemental oxygen and pressurized air, in accordance with embodiments of the present disclosure.

In the embodiment depicted in FIG. 4, control system 44 and/or other components of breathing assistance device 10 may be configured to hold the ratio of the supplemental oxygen flow $F_{oxygen}$ to the pressurized air flow $F_{air}$ constant during a first portion of the inhalation time $T_1$ then the reduce the ratio for a second portion of the inhalation time $T_2$, where $T_{inh}=T_1+T_2$, such that the concentration of oxygen during $T_1$ is greater than that of $T_2$. In certain embodiments, $F_{oxygen}$ may be reduced to zero for $T_2$, such that $F_{tot}=F_{air}$ during $T_2$. In other embodiments, $F_{oxygen}$ may be reduced to some non-zero flow rate.

The periods $T_1$ and $T_2$ and the flows $F_{oxygen}$, $F_{air}$, and $F_{tot}$ may be selected and/or determined in any suitable manner. For example, the periods $T_1$ and $T_2$ and/or the ratio of period $T_1$ to period $T_2$ may be determined experimentally. In addition, the flows $F_{oxygen}$, $F_{air}$, and $F_{tot}$ and/or the ratios of $F_{oxygen}$ to $F_{air}$ may be determined experimentally, and may be based on the desired effective oxygen concentration of the gas to be delivered to patient 30. In certain embodiments, the periods $T_1$ and $T_2$, the ratio of period $T_1$ to period $T_2$, the flows $F_{oxygen}$, $F_{air}$, and $F_{tot}$, and/or the ratios of $F_{oxygen}$ to $F_{air}$ may be set by a manufacturer of breathing assistance device 10. In other embodiments, such parameters may be set and/or adjusted by patient 30, a caregiver of patient 30, and/or another person. In certain embodiments, the periods $T_1$ and $T_2$ and the flows $F_{oxygen}$, $F_{air}$, and $F_{tot}$ may be selected that that the average oxygen concentration of the breathable gas delivered during the period $T_1$ is between approximately 22% and approximately 100%.

In a particular embodiment, $T_1$ and $T_2$ may be selected such that $T_1=\frac{2}{3}T_{inh}$ and $T_2=\frac{1}{3}T_{inh}$. If $F_{tot}=F_{air}$ during $T_2$ of such particular embodiment, such particular embodiment of FIG. 4 may provide an oxygen savings of approximately one-third compared with traditional approaches.

In the embodiment depicted in FIG. 5, control system 44 and/or other components of breathing assistance device 10 may reduce the ratio of the supplemental oxygen flow $F_{oxygen}$ to the pressurized air flow $F_{air}$ during a first portion of the inhalation time $T_1$, then hold the ratio constant for a second portion of the inhalation time $T_2$ (where $T_{inh}=T_1+T_2$). In certain embodiments, the ratio of the supplemental oxygen flow $F_{oxygen}$ to the pressurized air flow $F_{air}$ during the second portion $T_2$ may substantially equal the ratio of the supplemental oxygen flow $F_{oxygen}$ to the pressurized air flow $F_{air}$ at the end of the first portion $T_1$.

As shown in FIG. 5, $F_{oxygen}$ may have an initial value at the beginning of period $T_1$ that decreases to a final value during the period $T_1$, while $F_{air}$ may have an initial value of the beginning of period $T_1$ that increases to a final value during the period $T_1$. In certain embodiments, $F_{oxygen}$ may decrease at the same rate as $F_{air}$ increases during $T_1$, such that $F_{tot}$ remains constant during $T_1$. The decrease of $F_{oxygen}$ during $T_1$ and/or the increase of $F_{air}$ during $T_1$ may be linear or may be controlled according to any suitable function. In a particular embodiment, $F_{oxygen}$ may be equal to $F_{tot}$ at the beginning of $T_1$. In the same or alternative embodiments, $F_{oxygen}$ may decrease to zero during $T_1$, such that $F_{air}=F_{tot}$ at the end of $T_1$ and during $T_2$. In other embodiments, $F_{oxygen}$ may be reduced to some non-zero flow rate.

In the embodiment depicted in FIG. 5, the periods $T_1$ and $T_2$ and the flows $F_{oxygen}$, $F_{air}$, and $F_{tot}$ may be selected and/or determined in any suitable manner such that the concentration of oxygen during $T_1$ is greater than that of $T_2$. For example, the periods $T_1$ and $T_2$ and/or the ratio of period $T_1$ to period $T_2$ may be determined experimentally. In addition, the flows $F_{oxygen}$, $F_{air}$, and $F_{tot}$ and/or the ratios of $F_{oxygen}$ to $F_{air}$ may be determined experimentally, and may be based on the desired average oxygen concentration of the gas to be delivered to patient 30. In certain embodiments, the periods $T_1$ and $T_2$, the ratio of period $T_1$ to period $T_2$, the flows $F_{oxygen}$, $F_{air}$, and $F_{tot}$, and/or the ratios of $F_{oxygen}$ to $F_{air}$ may be set by a manufacturer of breathing assistance device 10. In other embodiments, such parameters may be set and/or adjusted by patient 30, a caregiver of patient 30, and/or another person. In certain embodiments, the periods $T_1$ and $T_2$ and the flows $F_{oxygen}$, $F_{air}$, and $F_{tot}$ may be selected that that the average oxygen concentration of the breathable gas delivered during the period $T_1$ is between approximately 22% and approximately 100%.

In a particular embodiment, $T_1$ and $T_2$ may be selected such that $T_1=\frac{2}{3}T_{inh}$ and $T_2=\frac{1}{3}T_{inh}$. If $F_{tot}=F_{air}$ during $T_2$ of such particular embodiment, such particular embodiment of FIG. 5 may provide an oxygen savings of approximately one-third compared with traditional approaches.

In the embodiment depicted in FIG. 6, control system 44 and/or other components of breathing assistance device 10 may be configured to deliver alternating pulses of supplemental oxygen and pressurized air during a first portion of the inhalation time $T_1$, and may hold the ratio of the supplemental oxygen flow $F_{oxygen}$ to the pressurized air flow $F_{air}$ constant for a second portion of the inhalation time $T_2$, where $T_{inh}=T_1+$ $T_2$, such that the concentration of oxygen during $T_1$ is greater than that of $T_2$. In certain embodiments, $F_{oxygen}$ may be held at zero for $T_2$, such that $F_{tot}=F_{air}$ during $T_2$. In other embodiments, $F_{oxygen}$ may be reduced to some non-zero flow rate. Although FIG. 6 depicts that the pulse widths of the alternating pulses of supplemental oxygen and pressurized air during $T_1$ may be equal, the pulse widths of supplemental oxygen and pressurized air may be different to permit delivery of a desired average oxygen concentration of gas delivered during $T_1$ such that the ratio of the pulse widths of the pulses of the pressurized oxygen to the pulse widths of the pulses of pressurized air are proportional to the desired oxygen concentration of the breathable gas.

In the embodiment depicted in FIG. 6, the periods $T_1$ and $T_2$ and the flows $F_{oxygen}$, $F_{air}$, and $F_{tot}$ may be selected and/or determined in any suitable manner. For example, the periods $T_1$ and $T_2$ and/or the ratio of period $T_1$ to period $T_2$ may be determined experimentally. In addition, the flows $F_{oxygen}$, $F_{air}$, and $F_{tot}$ and/or the pulse widths of $F_{oxygen}$ to $F_{air}$ may be determined experimentally, and may be based on the desired average oxygen concentration of the gas to be delivered to patient 30. In certain embodiments, the periods $T_1$ and $T_2$, the ratio of period $T_1$ to period $T_2$, the flows $F_{oxygen}$, $F_{air}$, and $F_{tot}$, and/or the pulse widths of $F_{oxygen}$ to $F_{air}$ may be set by a manufacturer of breathing assistance device 10. In other embodiments, such parameters may be set and/or adjusted by patient 30, a caregiver of patient 30, and/or another person. In certain embodiments, the periods $T_1$ and $T_2$ and the flows $F_{oxygen}$, $F_{air}$, and $F_{tot}$ may be selected that that the average oxygen concentration of the breathable gas delivered during the period $T_1$ is between approximately 22% and approximately 100%.

In a particular embodiment, $T_1$ and $T_2$ may be selected such that $T_1=\frac{2}{3}T_{inh}$ and $T_2=\frac{1}{3}T_{inh}$. If $F_{tot}=F_{air}$ during $T_2$ of such particular embodiment, such particular embodiment of FIG. 6 may provide an oxygen savings of approximately one-third compared with traditional approaches.

Although FIGS. 4-6 depict particular waveforms for $F_{oxygen}$, $F_{air}$, and $F_{tot}$, each of the waveforms may be defined by any suitable function such that the concentration of oxygen during a beginning portion of inhalation (e.g., $T_1$) is greater than that during a later portion of inhalation (e.g., $T_2$).

Although the disclosed embodiments have been described in detail, it should be understood that various changes, substitutions and alterations can be made to the embodiments without departing from their spirit and scope.

What is claimed is:

1. A breathing assistance device comprising:
a gas delivery system configured to supply breathable gas comprising air received from a pressurized air source and supplemental oxygen received from a supplemental oxygen source that is separate from the pressurized air source;
a patient interface configured to interface with a patient for delivering the breathable gas to one or more breathing passages of the patient;
a connection system configured to communicate the breathable gas supplied by the gas delivery system to the patient interface for delivery to the patient;
a control system configured to control the delivery of the breathable gas to the patient, the gas delivery system being configured to deliver the breathable gas with a first average oxygen concentration during a first portion of an inhalation phase for the patient, the gas delivery system being configured deliver the breathable gas with a second average oxygen concentration during a second portion of the inhalation phase for the patient, the second average oxygen concentration being lower than the first average oxygen concentration; and
a user interface connected to the control system, the use interface configured to receive characteristics of the patient from a user, the user interface configured to transmit the characteristics of the patient to the control system, the control system delivering the breathable gas to the patient during the inhalation phase based on the characteristics of the patient.

2. A system according to claim 1, wherein the supplemental oxygen source is prevented from sending the supplemental oxygen to the gas delivery system during the second portion of the inhalation phase for the patient.

3. A system according to claim 1, wherein the first average oxygen concentration of the breathable gas delivered during the first portion of the inhalation phase is between approximately 22% and approximately 100%.

4. A system according to claim 1, wherein the first portion of the inhalation phase comprises approximately two-thirds of the inhalation phase.

5. A system according to claim 1, wherein the gas delivery system is configured to deliver breathable gas with a substantially constant oxygen concentration during the first portion of the inhalation phase.

6. A system according to claim 1, wherein:
the gas delivery system is configured to deliver breathable gas with a continuously decreasing oxygen concentration during the first portion of the inhalation phase;
the pressurized air source is configured to send the air with a continuously increasing concentration of the air to the gas delivery system during the first portion of the inhalation phase; and
the supplemental oxygen source is configured to deliver a continuously decreasing concentration of the supplemental oxygen to the gas delivery system during the first portion of the inhalation phase.

7. A system according to claim 6, wherein the first oxygen concentration decreases linearly during the first portion of the inhalation phase.

8. A system according to claim 6, wherein the first oxygen concentration at the beginning of the first portion of the inhalation phase is approximately 100%.

9. A system according to claim 6, wherein the supplemental oxygen source is prevented from sending the supplemental oxygen to the gas delivery system at the end of the first portion of the inhalation phase.

10. A system according to claim 1, wherein the gas delivery system is configured to deliver alternating pulses of pressurized air and supplemental oxygen during the first portion of the inhalation phase.

11. A system according to claim 10, wherein the pulse widths of the pulses of pressurized air are approximately equal to the pulse widths of the pulses of supplemental oxygen.

12. A system according to claim 10, wherein the ratio of the pulse widths of the pulses of the supplemental oxygen to the pulse widths of the pulses of pressurized air are proportional to the desired oxygen concentration of the breathable gas.

13. A system according to claim 1, wherein the breathing assistance device is adapted to provide at least one of continuous positive airway pressure (CPAP) and bi-level CPAP to the patient.

14. A system according to claim 1, wherein the breathing assistance device is adapted to provide ventilation support to the patient.

15. A system according to claim 1, wherein the first average oxygen concentration and the second average oxygen concentration depend on a lung capacity of the patient and amount of oxygenation desired for the patient.

16. A system according to claim 1, wherein the characteristics of the patient comprise at least: age, weight, tidal volume, respiratory rate, inhale sensitivity, exhale sensitivity, circuit leak, rise time, alarm settings, delay, ramp, starting pressure, and an inhalation to exhalation ratio.

17. A system according to claim 1, further comprising:
a pressure detector connected to the control system, the pressure detector configured to determine a pressure of the breathable gas being provided to the patient; and
a flow detector configured to detect a flow of air being sent out by the pressurized air source,
wherein the gas delivery system delivers the breathable gas based on the pressure of the breathable gas and the flow of air sent out by the pressurized air source.

18. A method for delivering breathable gas to a patient comprising:
delivering, by a gas delivery system, a breathable gas comprising pressurized air received from a pressurized air source and supplemental oxygen received from a supplemental oxygen source that is separate from the pressurized air source, the breathable gas having a first average oxygen concentration during a first portion of an inhalation phase for a patient; and
delivering, by the gas delivery system, the breathable gas with a second average oxygen concentration during a second portion of an inhalation phase for a patient,
wherein the first average oxygen concentration and the second oxygen concentration are determined by the gas delivery system based on a pressure of the breathable gas detected by a pressure detector within the gas delivery system, and at least one of: a flow of at least one of the pressurized air and the supplemental oxygen detected by a flow detector within the gas delivery system, and one or more characteristics of the patient input by a user on a user interface associated with the gas delivery system.

19. A method according to claim 18, wherein the second average oxygen concentration is approximately equal to the oxygen concentration of pressurized air.

20. A method according to claim 18, wherein the average oxygen concentration of the breathable gas delivered during the first portion is between approximately 22% and approximately 100%.

21. A method according to claim 18, wherein the first portion of the inhalation phase comprises approximately two-thirds of the inhalation phase.

22. A method according to claim 18, further comprising delivering breathable gas with a substantially constant oxygen concentration during the first portion of the inhalation phase.

23. A method according to claim 18, further comprising decreasing the oxygen concentration of the breathable gas during the first portion of the inhalation phase.

24. A method according to claim 23, further comprising linearly decreasing the oxygen concentration of the breathable gas during the first portion of the inhalation phase.

25. A method according to claim 23, further comprising delivering breathable gas with an oxygen concentration of approximately 100% at the beginning of the first portion of the inhalation phase.

26. A method according to claim 23, further comprising delivering 5 breathable gas with an oxygen concentration approximately equal to the oxygen concentration of pressurized air at the end of the first portion of the inhalation phase.

27. A method according to claim 18, further comprising delivering alternating pulses of pressurized air and supplemental oxygen during the first portion of the inhalation phase.

28. A method according to claim 27, wherein the pulse widths of the pulses of pressurized air are approximately equal to the pulse widths of the pulses of supplemental oxygen.

29. A method according to claim 27, wherein the ratio of the pulse widths of the pulses of the pressurized oxygen to the pulse widths of the pulses of pressurized air are proportional to the desired oxygen concentration of the breathable gas.

30. A method according to claim 18, wherein a breathing assistance device delivering the breathable gas is adapted to provide at least one of continuous positive airway pressure (CPAP) and bi-level CPAP to the patient.

31. A method according to claim 18, wherein a breathing assistance device delivering the breathable gas is adapted to provide ventilation support to the patient.

* * * * *